United States Patent
Christie et al.

(10) Patent No.: US 6,747,102 B1
(45) Date of Patent: Jun. 8, 2004

(54) METHOD FOR RADICAL AQUEOUS EMULSION POLYMERIZATION

(75) Inventors: David Christie, Mannheim (DE); Jerome Claverie, Lyons (FR); Saba Kanagasabapathy, Lyons (FR)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/926,250

(22) PCT Filed: Mar. 23, 2000

(86) PCT No.: PCT/EP00/02566

§ 371 (c)(1), (2), (4) Date: Oct. 1, 2001

(87) PCT Pub. No.: WO00/59954

PCT Pub. Date: Oct. 12, 2000

(30) Foreign Application Priority Data

Apr. 1, 1999 (DE) .......................................... 199 14 953

(51) Int. Cl.$^7$ .............................. C08F 2/24; C08F 2/38; C07C 251/16
(52) U.S. Cl. .......................... 526/93; 526/100; 524/800
(58) Field of Search ............................ 524/800; 526/93, 526/100

(56) References Cited

U.S. PATENT DOCUMENTS

| | | |
|---|---|---|
| 4,680,352 A | 7/1987 | Janowicz et al. |
| 5,312,871 A | 5/1994 | Mardare et al. |
| 5,763,548 A | 6/1998 | Matyjaszewski et al. |
| 5,811,500 A | 9/1998 | Dubois et al. |

FOREIGN PATENT DOCUMENTS

| | | | |
|---|---|---|---|
| EP | 0 714 416 | 6/1996 | |
| EP | 0 841 346 | 5/1998 | |
| GB | 1199387 | 7/1970 | |
| JP | 74011468 B | * 3/1974 | ............. C08F/1/11 |
| WO | WO 87/03605 | 6/1987 | |
| WO | WO 95/04759 | 2/1995 | |
| WO | WO 96/15158 | 5/1996 | |
| WO | WO 98/50436 | 11/1998 | |

OTHER PUBLICATIONS

B. B. Wayland, et al., J. Am. Chem. Soc., vol. 116, No. 17, pp. 7943–7944, "Living Radical Polymerization of Acrylates by Organocobalt Porphyrin Complexes", 1994.

Research Disclosure, No. 416, pp. 1595–1604, Dec. 1998.

T. Makino, et al., American Chemical Society, Polymer Chemistry Division, Polymer Preprints, vol. 39, No. 1, pp. 288–289, "Controlled Atom Transfer Radical Polymerizarions of Methyl Methacrylate Under Micellar Conditions", Mar. 1998.

S. G. Gaynor, et al., Macromolecules, vol. 31, No. 17, pp. 5951–5954, "Controlled/"Living" Radical Polymerization Applied to Water–Borne Systems", Aug. 25, 1998.

* cited by examiner

*Primary Examiner*—Kelechi C. Egwim
(74) *Attorney, Agent, or Firm*—Oblon, Spivak, McClelland, Maier & Neustadt, P.C.

(57) ABSTRACT

In a process for the free radical-initiated aqueous emulsion polymerization for the preparation of an aqueous polymer dispersion, ethylenically unsaturated monomers are polymerized by means of a free radical polymerization initiator in the presence of organometallic compounds having a controlling effect.

16 Claims, 5 Drawing Sheets

Figure 1: Dependence of the number average molecular weight ($M_n$) on the styrene conversion (C)

C (% by weight)

Figure 2: Dependence of the number average molecular weight ($M_n$) on the styrene conversion (C)

C (% by weight)

Figure 3: Dependence of the number average molecular weight ($M_n$) on the MMA conversion (C)

C (% by weight)

Figure 4: Dependence of the number average molecular weight ($M_n$) on the MMA conversion (C)

C (% by weight)

Figure 5: Dependence of the number average molecular weight ($M_n$) on the MMA conversion (C)

C (% by weight)

METHOD FOR RADICAL AQUEOUS EMULSION POLYMERIZATION

The present invention relates to a process for free radical-initiated aqueous emulsion polymerization for the preparation of an aqueous polymer dispersion, in which at least one chemical compound (monomer) having at least one ethylenically unsaturated group is dispersed in an aqueous medium and polymerized by means of at least one free radical polymerization initiator in the presence of at least one organometallic compound.

Controlled polymerization reactions open up the possibility of synthesizing polymers having a specific molecular structure, defined molecular weight and low polydispersity and thus establishing a specific property profile of said polymers. In the last 40 years, a large number of methods which were essentially based on anionic and cationic mechanisms have been developed for this purpose (cf. O. W. Webster in Science 1991, 251, pages 887 to 893).

Compared with the ionic polymerization variants free radical polymerization reactions have the fundamental advantage that they can be carried out with a larger number of commercially important monomers and moreover can be effected by mass, solution, suspension and emulsion polymerization. However, attempts to find suitable catalysts for controlled free radical polymerization reactions have for a long time been unsuccessful.

It recently became known that N-oxyl radicals may be suitable for controlling free radical-initiated polymerization reactions of ethylenically unsaturated monomers. In this context, reference may be made, for example, to U.S. Pat. No. 4,581,429, EP-A 735 052, WO 94/11412, U.S. Pat. No. 5,322,912, U.S. Pat. No. 5,412,047 and GB 1 124 009.

The fact that organic metal complexes, too, are capable of controlling free radical polymerization processes is described by Wayland et al. in J. Am. Chem. Soc. 1994, 116, pages 7943 to 7944, for the controlled free radical solution polymerization of arylates using specific cobalt-porphyrin complexes, by way of example.

U.S. Pat. No. 5,312,871 discloses the use of a catalyst system for the controlled polymerization of ethylenically unsaturated monomers, consisting of an alkyl- or aryl-metal compound, an organic ligand and a stable radical. EP-A 841 346 discloses specific cobalt, rhodium and iridium complexes for controlling free radical polymerization reactions of ethylenically unsaturated monomers.

Application WO 87/03605 discloses the preparation of oligomeric compounds. The oligomers are prepared by free radical polymerization of ethylenically unsaturated monomers using specific transition metal catalysts. The preparation of aqueous polymer dispersions by means of free radical-initiated aqueous emulsion polymerization is, however, not disclosed.

Research Disclosure, December 1998, 416, pages 1595 to 1604, describes the controlling effect of specific porphyrin-, phthalocyanine- and salen-iron complexes in the solution and mass polymerization of styrene. In addition to the azobisisobutyronitrile used as free radical initiator, substituted alkyl bromides are used as polymerization initiator. The porphyrin-, phthalocyanine- or salen-iron complexes are always present in less than the molar stoichiometric amount relative to the substituted alkyl bromide used as a free radical polymerization initiator. Free radical aqueous emulsion polymerizations are not included.

In a corresponding manner, EP-A 714 416 discloses the use of specific cobalt complexes with tetradentate nitrogen ligands for controlling free radical polymerization reactions both in solution and in emulsion. The free radical initiators used are, exclusively, substituted aliphatic azo compounds.

U.S. Pat. No. 5,763,548 likewise discloses a process for controlled free radical polymerization, in which the controlling effect of organometallic compounds is employed.

WO 98/50436 describes the controlling effect of specific cobalt-oxime/boron fluoride complexes in free radical-initiated aqueous emulsion polymerization. Characteristic of the disclosed process is that hydrophobic solvents, for example higher alkanes or fatty alcohols for taking up the cobalt complex, are required in addition to the monomers.

Makino et al. disclose, in Polymer Preprints Vol. 39, March 1998, 288 and 289 (Am. Chem. Soc.; Polymer Chemistry Division), a process for the controlled free radical aqueous emulsion polymerization of ethyl methacrylate. The polymerization initiator used is ethyl 2-bromoisobutanoate. Furthermore, the emulsion polymerization is carried out in the presence of a relatively water-soluble copper(I)-bispyridyl complex. The molar ratio of the polymerization initiator used to the water-soluble copper(I)-bispyridyl complex is 1:1. The dispersant used is sodium dodecyl sulfate.

According to Matyjaszewski et al., Macromolecules 1998, 31, 5951 to 5954, the results obtained by Makino et al. are unsatisfactory. This is because, on the one hand, the copper(I)-bispyridyl complex is said to have much too high a water solubility and in addition the combination $Cu^{2+}/SO_4^{2-}$ is said to be completely disadvantageous for a controlling effect. Matyjaszewski et al. therefore recommend using nonionic polyethylene glycol oleyl ethers as dispersants and water-insoluble copper(I)-dialkylbispyridyl complexes as organometallic compounds.

In view of the above prior art, it is an object of the present invention to provide a process for controlled free radical aqueous emulsion polymerization, in which organometallic compounds other than those in the processes of the prior art exercise the controlling effect and which, in particular in the presence of sodium dodecyl sulfate as a dispersant, results in satisfactory control and furthermore does not require the presence of a hydrophobic organic solvent and requires no special polymerization initiators.

We have found that this object is achieved by a process for free radical-initiated aqueous emulsion polymerization for the preparation of an aqueous polymer dispersion, in which at least one monomer having at least one ethylenically unsaturated group is dispersed in an aqueous medium and polymerized by means of at least one free radical polymerization initiator in the presence of at least one organometallic compound, wherein the at least one organometallic compound on the one hand has the following structural feature of the formula I,

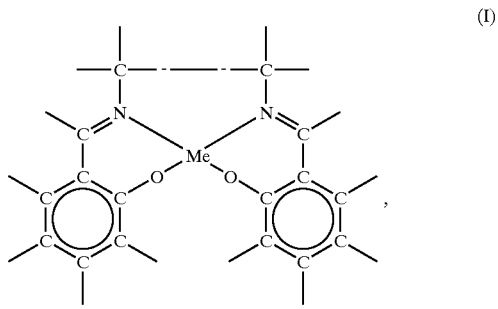

where:

| | |
|---|---|
| Me | is a metal ion, |
| —.—.— | is a covalent bond or a monoatomic to triatomic covalent, bridging chain, the atoms bonded to the chain members not being included, and |
| — | is a covalent bond to a neighboring atom, | and, on the otherhand, is such that at 20° C. and 1 bar (absolute) its solubility in acidic, basic and/or neutral water is greater than its solubility in styrene.

The procedure for a free radical-initiated aqueous emulsion polymerization of monomers having at least one ethylenically unsaturated group has often been described in the past and is therefore sufficiently well known to a person skilled in the art [cf. for example Encyclopedia of Polymer Science and Engineering, Vol. 8, page 659 et seq. (1987); D. C. Blackley, in High Polymer Latices, Vol. 1, page 35 et seq. (1966); H. Warson, The Applications of Synthetic Resin Emulsions, page 246 et seq., Chapter 5 (1972); D. Diederich, Chemie in unserer Zeit 24, page 135 to 142 (1990); Emulsion Polymerization, Interscience Publishers, New York (1965); DE-A 40 03 422 and Dispersionen synthetischer Hochpolymerer, F. Hölscher, Springer-Verlag, Berlin (1969)]. It is usually carried out by dispersing the at least one monomer, frequently in the presence of dispersants, in an aqueous medium and polymerizing it by means of a free radical polymerization initiator. The novel process differs from the procedure only in the additional presence of at least one organometallic compound which has the structural feature of formula I.

Monomers having at least one ethylenically unsaturated group which are suitable for the novel process include in particular monomers capable of free radical polymerization in a simple manner, for example ethylene, vinylaromatic monomers such as styrene, α-methyl styrene, o-chlorostyrene or vinyltoluenes, esters of vinyl alcohol and monocarboxylic acids of 1 to 18 carbon atoms such as vinyl acetate, vinyl propionate, vinyl n-butyrate, vinyl laurate and vinyl stearate, esters of α,β-monoethylenically unsaturated mono- and dicarboxylic acids, preferably of 3 to 6 carbon atoms, in particular acrylic acid, methacrylic acid, maleic acid, fumaric acid and itaconic acid, with alkanols of in general 1 to 12, preferably 1 to 8, in particular 1 to 4, carbon atoms, in particular methyl, ethyl, n-butyl, isobutyl and 2-ethylhexyl acrylate and methacrylate, dimethyl maleate or di-n-butyl maleate, nitriles of α,β-monoethylenically unsaturated carboxylic acids, such as acrylonitrile, and conjugated $C_{4-8}$-dienes, such as 1,3-butadiene and isoprene. Said monomers are as a rule the main monomers which usually together account for more than 50% by weight, based on the total amount of the monomers to be polymerized by the novel free radical aqueous emulsion polymerization process. As a rule, these monomers have only moderate to low solubility in water under standard conditions of temperature and pressure (25° C., 1 bar).

Monomers which have higher water solubility under the abovementioned conditions are, for example, α,β-monoethylenically unsaturated mono- and dicarboxylic acids and their amides, e.g. acrylic acid, methacrylic acid, maleic acid, fumaric acid, itaconic acid, acrylamide and methacrylamide, and further vinylsulfonic acid and its water-soluble salts and N-vinylpyrrolidone.

Usually, the abovementioned monomers are incorporated by polymerization only as modifying monomers in amounts of less than 50, as a rule from 0.5 to 20, preferably from 1 to 10%, by weight, based on the total amount of the monomers to be polymerized.

Monomers which usually increase the internal strength of the films of the aqueous polymer dispersions usually have at least one epoxy, hydroxyl, N-methylol or carbonyl group or at least two non-conjugated ethylenically unsaturated double bonds. Examples of these are N-alkylolamides of α,β-monoethylenically unsaturated carboxylic acids of 3 to 10 carbon atoms, among which N-methylolacrylamide and N-methylolmethacrylamide are very particularly preferred, and their esters with alkanols of 1 to 4 carbon atoms. Monomers having two vinyl radicals, monomers having two vinylidene radicals, and monomers having two alkenyl radicals are also suitable. The diesters of dihydric alcohols with α,β-monoethylenically unsaturated monocarboxylic acids are particularly advantageous, among which acrylic or methacrylic acids are preferred. Examples of such monomers having two nonconjugated ethylenically unsaturated double bonds are alkylene glycol diacrylates and dimethacrylates, such as ethylene glycol diacrylate, 1,2-propylene glycol diacrylate, 1,3-propylene glycol diacrylate, 1,3-butylene glycol diacrylate, 1,4-butylene glycol diacrylates and ethylene glycol dimethacrylate, 1,2-propylene glycol dimethacrylate, 1,3-propylene glycol dimethacrylate, 1,3-butylene glycol dimethacrylate and 1,4-butylene glycol dimethacrylates, and divinylbenzene, vinyl methacrylate, vinyl acrylate, allyl methacrylate, allyl acrylate, diallyl maleate, diallyl fumarate, methylenebisacrylamide, cyclopentadienyl acrylate or triallyl cyanurate. The $C_1$–$C_8$-hydroxyalkyl methacrylates and acrylates, such as n-hydroxyethyl, n-hydroxypropyl- or n-hydroxybutyl acrylate and methacrylate, and compounds such as diacetoneacrylamide and acetylacetoxyethyl acrylate and methacrylate, are also particularly important in this context. In the case of aqueous emulsion polymer dispersions produced exclusively by the free radical aqueous emulsion polymerization method, the abovementioned monomers are incorporated by polymerization generally in amounts from 0.5 to 10% by weight, based on the total amount of the monomers to be polymerized.

The molar ratio of the ethylenically unsaturated monomers used for the free radical novel aqueous emulsion polymerization to the at least one organometallic compound which contains the structural feature of the formula I is as a rule $\geq 1$, usually $\geq 10$, often $\geq 100$ and frequently $\geq 1000$.

Suitable free radical polymerization initiators for the novel free radical aqueous emulsion polymerization are all those which are capable of initiating a free radical aqueous emulsion polymerization without deactivating the at least one organometallic compound which has the structural feature I. In principle, they may be both peroxides and azo compounds. Of course, redox initiator systems are also suitable. In order to carry out the free radical aqueous emulsion polymerization particularly efficiently from the point of view of the desired properties and with respect to high cost-efficiency, the use of aliphatic azo compounds, for example azobisisobutyronitrile, as free radical initiator is preferred. The amount of the free radical polymerization initiator used is preferably from 0.1 to 2% by weight, based on the total amount of the monomers to be polymerized.

The manner in which the free radical polymerization initiator is added to the polymerization vessel in the course of the novel free radical aqueous emulsion polymerization seems to be of minor importance. The polymerization initiator may be either initially introduced completely into the polymerization vessel or added continuously or stepwise at the rate of its consumption in the course of the free radical aqueous emulsion polymerization. Specifically, this depends, in a manner known per se to a person skilled in the art, inter alia on the chemical nature of the polymerization initiator, on the monomer system to be polymerized and on the polymerization temperature.

A direct consequence of the abovementioned fact is that the total range from 0 to 150° C. is suitable as a reaction temperature for the novel free radical aqueous emulsion polymerization, and temperatures of from 70 to 120° C., preferably from 80 to 100° C., particularly preferably from >85 to 100° C., are preferably used. The novel free radical aqueous emulsion polymerization can be carried out at less than, equal to or greater than 1 bar (absolute), so that the polymerization temperature may exceed 100° C. and may be up to 150° C. Preferably, readily volatile monomers, such as ethylene, butadiene or vinyl chloride, are polymerized under superatmospheric pressure. The pressure may be 1.2, 1.5, 2, 5, 10 or 15 bar or may assume even higher values. If emulsion polymerizations are carried out under reduced pressure, pressures of 950, frequently 900, often 850, mbar (absolute) are established. The free radical aqueous emulsion polymerization is advantageously carried out at 1 bar (absolute) under an inert gas atmosphere, for example under nitrogen or argon.

For the purposes of the invention, instead of or in addition to the abovementioned free radical polymerization initiators, at least one compound of the formula III can also advantageously be used as a free radical polymerization initiator:

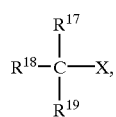

(III)

where:

X is an element from the group consisting of —Cl, —Br, —I, —OR$^{20}$, where R$^{20}$ is C$_1$- to C$_{20}$-alkyl, in which up to one third of the H atoms may, independently of one another, be replaced by —Cl, —Br and —I, —SR$^{21}$, —SeR$^{21}$, —OC(=O)R$^{21}$, —OP(=O)R$^{21}$, —OP(=O)(OR$^{21}$)$_2$, —OP(=O)OR$^{21}$, —ON(R$^{21}$)$_2$, —SC(=S)N(R$^{21}$)$_2$, —SC(=S)R$^{21}$, where R$^{21}$ is -aryl or C$_1$- to C$_{20}$-alkyl and, in the case of —ON(R$^{21}$)$_2$, the two groups R$^{21}$ with the N atom carrying them may form a 5- or 6-membered heterocyclic ring, and R$^{17}$, R$^{18}$, R$^{19}$ independently of one another, are each —H, —Cl, —Br, —I, —CO$_2$H, —CN, —CO$_2$R$^{21}$, C$_1$- to C$_{20}$-alkyl, which may be unsubstituted or substituted, C$_3$- to C$_8$-cycloalkyl, which may be unsubstituted or substituted, -aryl, which may be unsubstituted or substituted, -aralkyl, which may be unsubstituted or substituted, or heterocyclyl, which may be unsubstituted or substituted.

If the free radical polymerization initiators used are compounds of the formula III, compounds where X is —Cl, —Br and —I are preferred.

The molar ratio of the at least one organometallic compound which contains the structural feature of the formula I to the at least one free radical polymerization initiator is dependent on, inter alia, the ethylenically unsaturated monomers which are used for the aqueous emulsion polymerization, on the size and the geometry of the reaction container and on whether a portion or the total amount of the ethylenically unsaturated monomers is initially taken in the aqueous reaction medium and the remaining amount is fed continuously or batchwise to the aqueous emulsion medium at the rate of consumption, on which free radical polymerization initiator and which organometallic compound which contains the structural feature of formula I are used or on whether a portion or the total amount of the at least one organometallic compound is initially taken in the aqueous reaction medium and the remaining amount is fed in continuously or batchwise in the course of the polymerization. An advantageous molar ratio of the at least one organometallic compound which contains the structural feature of the formula I to the at least one free radical polymerization initiator can be rapidly determined by a person skilled in the art for the respective system in preliminary experiments which are easy to carry out. It is usually from 0.00001:1 to 10:1, frequently from 0.001:1 to 1:1, often from 0.05:1 to 0.5:1. If exclusively free radical polymerization initiators of the formula III are used, the at least one organometallic compound which contains the structural feature of the formula I can be used for the free radical aqueous emulsion polymerization in less than the molar stoichiometric amount.

Usually, dispersants which keep both the monomer droplets and polymer particles dispersed in the aqueous phase and thus ensure the stability of the aqueous polymer dispersion produced are present during the novel free radical aqueous emulsion polymerization. Suitable dispersants of this type are both the protective colloids usually used for carrying out free radical aqueous emulsion polymerizations and emulsifiers.

Suitable protective colloids are, for example, polyvinyl alcohols, cellulose derivatives or vinylpyrrolidone-containing copolymers. A detailed description of further suitable protective colloids is to be found in Houben-Weyl, Methoden der organischen Chemie, Volume XIV/1, Makromolekulare Stoffe, Georg-Thieme-Verlag, Stuttgart, 1961, pages 411 to 420. Of course, mixtures of emulsifiers and/or protective colloids can also be used. Preferably used dispersants are exclusively emulsifiers whose relative molecular weights, in contrast to the protective colloids, are usually less than 1000. They may be anionic, cationic or nonionic. Where mixtures of surfactants are used, the initial components must of course be compatible with one another, which can be checked by means of a few preliminary experiments in case of doubt. In general, anionic emulsifiers are compatible with one another and with nonionic emulsifiers. The same also applies to cationic emulsifiers, whereas anionic and cationic emulsifiers are generally incompatible with one another. Conventional emulsifiers are, for example, ethoxylated mono-, di- and trialkylphenols (degree of ethoxylation: from 3 to 50, alkyl radical: C$_4$ to C$_{12}$), ethoxylated fatty alcohols (degree of ethoxylation: from 3 to 50; alkyl radical: C$_8$ to C$_{36}$) and alkali metal and ammonium salts of alkyl sulfates (alkyl radical: C$_8$ to C$_{12}$), of sulfuric monoesters of ethoxylated alkanols (degree of ethoxylation: from 4 to 30, alkyl radical: C$_{12}$ to C$_{18}$) and ethoxylated alkyl phenols (degree of ethoxylation: from 3 to 50, alkyl radical: C$_4$ to C$_{12}$), of alkylsulfonic acids (alkyl radical: C$_{12}$ to C$_{18}$) and of alkylarylsulfonic acids (alkyl radical: C$_9$ to C$_{18}$). Further suitable emulsifiers are to be found in Houben-Weyl, Methoden der organischen Chemie, Volume XIV/1, Makromolekulare Stoffe, Georg-Thieme-Verlag, Stuttgart, 1961, pages 192 to 208.

Furthermore, compounds of the formula IV

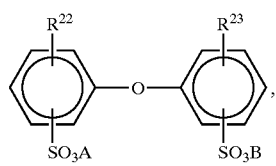

(IV)

where $R^{22}$ and $R^{23}$ are each H or $C_4$- to $C_{24}$-alkyl and are not simultaneously H, and A and B may be alkali metal ions and/or ammonium ions, have proven to be surfactants. In the formula IV, $R^{22}$ and $R^{23}$ are preferably linear or branched alkyl of 6 to 18, in particular 6, 12 or 16, carbon atoms or —H, $R^{22}$ and $R^{23}$ not both being H simultaneously. A and B are preferably sodium, potassium or ammonium, sodium being particularly preferred. Compounds IV in which A and B are sodium, $R^{22}$ is a branched alkyl radical of 12 carbon atoms and $R^{23}$ is H or $R^{22}$ are particularly advantageous Frequently, industrial mixtures which contain from 50 to 90% by weight of monoalkylated product, for example Dowfax® 2A1 (trademark of Dow Chemical Company) are used. The compounds IV are preferably used as dispersants in the novel process by themselves or, particularly preferably, as a mixture with ethoxylated fatty alcohols (degree of ethoxylation: from 3 to 50, alkyl radical: $C_8$ to $C_{36}$). The compounds IV are generally known, for example, from U.S. Pat. No. 4,269,749, and are commercially available. As a rule, the amount of dispersant used is from 1 to 3% by weight, based on the monomers to be subjected to free radical polymerization.

Of course, the abovementioned dispersants are suitable very generally for carrying out the novel process. However, the novel process also comprises the preparation of aqueous polymer dispersions of self-emulsifying polymers, in which monomers which have ionic groups give rise to stabilization owing to repulsion of charges of the same sign.

Anionic dispersants are preferably used for the novel process.

In the free radical aqueous emulsion polymerization process according to the invention, the controlling effect is achieved in the free radical aqueous emulsion polymerization by polymerizing the monomers in the presence of at least one organometallic compound which contains the structural feature shown in the formula I. A good controlling effect of the at least one organometallic compound is evident from the fact that, as the degree of polymerization progresses, the number average molecular weight ($M_n$) of the polymer formed from the at least one monomer having at least one ethylenically unsaturated group increases linearly with the monomer conversion (C) and the straight line shown in the graph, formed from $M_n$ (ordinate) and a given C (abscissa), passes through the origin ($M_n$ and C equal 0) and the polymer formed moreover has a low polydispersity, calculated from the quotient of weight average molecular weight ($M_w$) and $M_n$.

Compounds of the formula II

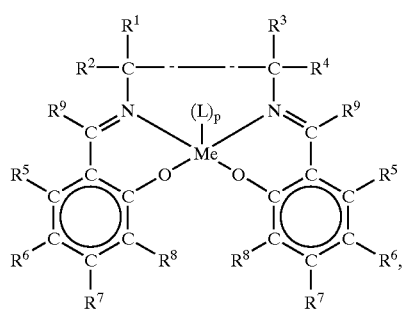

(II)

where:
$R^1$, $R^2$, $R^3$, $R^4$ independently of one another, are each —H, —$CO_2M^1$, where $M^1$ is —H, an alkali metal, ammonium or ($CH_2CH_2O$—$)_mM^2$, where $M^2$ is —H, an alkali metal or ammonium and m is from 1 to 1000, —$PO_3HM^1$, —$PO_3M^3M^4$, where $M^3$ and $M^4$ independently of one another are each an alkali metal, ammonium, $C_1$- to $C_{12}$-alkyl or substituted alkyl, in which up to four H atoms of the alkyl radical are replaced by —$OM^1$, —$SM^1$, —$CO_2M^1$, —$NH_2$, a quaternized nitrogen atom, —$SO_3M^1$ and/or —$OSO_3M^1$ or —$CH_2O$—($CH_2CH_2O$—$)_mM^2$ and moreover
$R^1$ and/or $R^3$ independently of $R^2$ and $R^4$, may be —CN, and
$R^2$ and $R^4$, together with the carbon atoms carrying them and directly linked by a covalent bond, independently of $R^1$ and $R^3$, can form an aliphatically saturated, an aliphatically partly unsaturated or an aromatically unsaturated ring which can additionally contain from 1 to 3 hetero atoms, selected from the group consisting of N, O, S and P, the number of ring atoms being from 5 to 10, and
$R^5$, $R^6$, $R^7$, $R^8$ independently of one another are each —H, —F, —Cl, —Br, —I, —$NO_2$, —CHO, —$SM^1$, —$OM^1$, —$SO_3M^1$, —$CO_2M^1$, —CN, —SCN, —$PO_3HM1$, —$PO_3M^3M^4$, —$OSO_3M^1$, —$OPO_3HM^1$, —$OPO_3M^3M^4$, —$NR^{10}R^{11}$, where $R^{10}$ and $R^{11}$, independently of one another, are each —H or $C_1$- to $C_6$-alkyl, —$SiR^{12}R^{13}R^{14}$, where $R^{12}$, $R^{13}$ and $R^{14}$, independently of one another, are each $C_1$- to $C_6$-alkyl or $C_1$- to $C_6$-alkoxy, —$OR^{15}$, —$SR^{15}$, —$CO_2R^{15}$, —$PO_3HR^{15}$, —$PO_3R^{15}R^{16}$, where $R^{15}$ and $R^{16}$, independently of one another, are each $C_1$- to $C_3$-alkyl or $C_2$- to $C_6$-alkyl, in which up to four H atoms of the alkyl radical are replaced by —$OM^1$, —$SM^1$, —$CO_2M^1$, —$NH_2$, a quaternized nitrogen atom, —$SO_3M^1$ and/or —$OSO_3M^1$, —$CH_2O$—($CH_2CH_2O$—$)_mM^2$, $C_1$- to $C_{10}$-alkyl, in which at least half the carbon atoms are replaced by at least one substituent from the group consisting of —$OM^1$, —$SM^1$, —$CO_2M^1$, —$NH_2$, a quaternized nitrogen atom, —$SO_3M^1$ and —$OSO_3M^1$, $C_2$- to $C_{10}$-alkenyl, in which up to three H atoms are replaced by —$OM^1$, —$SM^1$, —$CO_2M^1$, —$NH_2$, a quaternized nitrogen atom, —$SO_3M^1$ and/or —$OSO_3M^1$, and moreover
two of the radicals $R^5$, $R^6$, $R^7$ and $R^8$, which are carried by neighboring carbon atoms, together with the carbon atoms carrying them and independently of the other radicals, can form an aliphatically saturated, an aliphatically partly unsaturated or an aromatically unsaturated ring which can additionally contain from 1 to 3 hetero atoms selected from the group consisting of N, O, S and P, the number of ring atoms being 5 or 6, and the two radicals $R^7$ and/or the two radicals $R^8$, in each case with the carbon atoms carrying these radicals, can form a 5- or 6-atom covalent, bridging chain, the atoms bonded to the chain members not being included, $R^9$ is —H, —.—.— is either a covalent bond or a covalent, bridging chain of up to three atoms, the atoms bonded to the chain members not being included, Me is a metal ion, L is a Lewis base and p is 0, 1 or 2.

are used as suitable one or more organometallic compounds containing the structural feature of the formula I.

Preferred organometallic compounds of the formula II are those in which the carbon atoms carrying $R^1$ and $R^2$ and $R^3$ and $R^4$ are bonded to one another directly by means of a covalent bond, and $R^1$ to $R^4$ are either H atoms or part of an unsubstituted or substituted benzene ring. Particularly preferred organometallic compounds of the formula II are those in which moreover at least one of the radicals $R^5$ to $R^8$ is OH. Especially preferred organometallic compounds of the formula II are those in which $R^7$ is OH. In particular, preferred organometallic compounds of the formula II are those in which the carbon atoms carrying $R^1$ and $R^2$ and $R^3$ and $R^4$ are bonded to one another directly by means of a covalent bond, $R^1$ to $R^4$ are either H atoms or, with the carbon atoms carrying them, are part of a benzene ring, $R^7$ is OH and $R^5$, $R^6$ and $R^8$ are each H atoms. The organometallic compound in which $R^1$ to $R^4$ are each H atoms is referred to as a hydroxysalen complex. If, on the other hand, $R^1$ to $R^4$, with the carbon atoms carrying them, are part of a benzene ring, the organometallic compound is referred to as a hydroxysaloph complex. If in both cases $R^7$ is likewise an H atom, the terms salen and saloph complexes, respectively, are used.

$Ce^{2+}$ and $Ce^{3+}$. Often, the metal ion is selected from the group consisting of $Fe^{2+}$, $Fe^{3+}$, $Co^{2+}$, $Co^{3+}$, $Cr^{2+}$, and $Cr^{3+}$. Frequently, the metal ion is used in the lower oxidation state.

Suitable Lewis bases L are, for example, water, tetrahydrofuran, dioxane, pyridine, ammonia, primary, secondary or tertiary aliphatic or aromatic amines, whose aliphatic or aromatic radicals may be substituted, and unsubstituted or substituted trialkyl-, trialkoxy-, triaryl- and triaryloxyphosphines. Depending on the metal ion Me, the radicals $R^1$ to $R^8$ and the conditions during the free radical aqueous emulsion polymerization, the number p of the co-ordinated Lewis bases L may be 0, 1 or 2.

The syntheses of the organometallic compounds of the formula II have often been described in the past and are therefore sufficiently well known to a person skilled in the art cf. in this context EP-A 362 139 and JP 1 090 150 and Yang et al. in Hecheng Huaxue 1995, 3(1), 75 et seq., Kasuaga et al. in Inorg. Chem. Acta 1989, 157, 267 et seq., Spiratos et al. in Rev. Roum. Chim. 1980, 25, 1083 et seq., Spiratos et al. in Rev. Roum. Chim. 1984, 29, 457 et seq., Fullerton and Ahern in Tetrahedron Lett. 1976, 139 et seq., Zelentsov and Somova in Zh. Obshch. Khim. 1974, 44(6), 1309 et seq., Vitalini et al. in Macromolecules 1996, 29, 4478 et seq., Gaber et al. in Egypt. J. Chem. 1992, 34, 107 et seq., Kanbayashi et al. in J. Chromatogr. 1987, 386, 191 et seq., Marcu et al. in Polym. Bull. 1986, 16(2–3), 103 et seq., Dorutiu et al. in Stud. Univ. Babes-Bolyai, [Ser.] Chem. 1980, 25(2), 49 et seq., Zelentsov and Somova in Zh. Neorg. Khim. 1973, 18(8) 2128 et seq. and Mukheriee and Ray in J. Indian Chem. Soc. (1955), 604, 606 and 607]. Usually, an aromatic hydroxycarbonyl compound of the formula V is reacted with a diamine of the formula VI according to the following reaction scheme to give a Schiff base reaction product of the formula VII, which in turn forms with the metal ion, virtually quantitatively, the organometallic compound of the formula II:

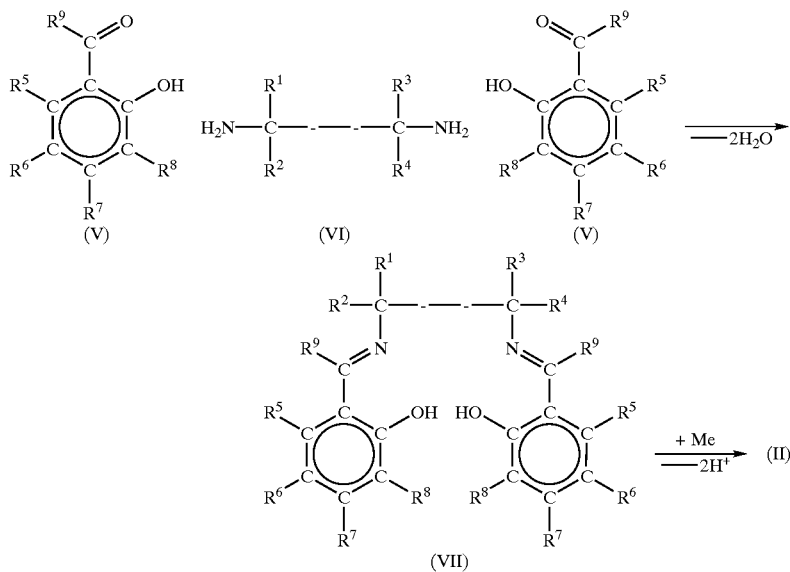

Me is preferably a metal ion which can occur reversibly in at least two oxidation states. Me is advantageously selected from the group consisting of $Fe^{2+}$, $Fe^{3+}$, $Ru^{2+}$, $Ru^{3+}$, $Cr^{2+}$, $Cr^{3+}$, $Mo^{2+}$, $Mo^{3+}$, $W^{2+}$, $W^{3+}$, $Co^{2+}$, $Co^{3+}$, $Re^{2+}$, $Re^{3+}$, $V^{2+}$, $V^{3+}$, $Mn^{2+}$, $Mn^{3+}$, $Zr^{2+}$, $Zr^{3+}$, $Zr^{4+}$, $Ti^{2+}$, $Ti^{3+}$, $Ti^{4+}$, At 1 bar (absolute) and 20° C., organometallic compounds of the formula II have a certain solubility in water an in organic solvents and in olefinically unsaturated monomers, of which styrene is a typical member. Their solubility in water can be significantly influenced by adding bases or acids. The use of organometallic compounds of the formula II whose solubility under the abovementioned conditions in 1000 g of acid, basic and/or neutral water is greater than their solubility in 1000 g of styrene is claimed according to the invention. In this publication, solubility is understood as meaning the maximum amount of dissolved organometallic compound of the formula II in grammes for 1000 g of solvent. UV/VIS spectroscopic methods are particularly suitable for determining the solubility of these organometallic compounds.

Organometallic compounds which are suitable according to the invention and contain the structural feature of the formula I have, as a rule, a solubility of $\leq 100$ g/1000 g, but often a solubility of $\geq 0.001$ g/1000 g and frequently $\geq 0.1$ g/1000 g in acidic, basic and/or neutral water at 1 bar (absolute) and 20° C. In styrene, said organometallic compounds have, as a rule, a solubility of $\leq 1$ g/1000 g, often $\leq 0.1$ g/1000 g and frequently $\leq 0.01$ g/1000 g under identical conditions.

The novel process can be carried out, for example, by initially taking either a portion or the total amount of the required water, of the required at least one organometallic compound containing the structural feature of the formula I, of the at least one polymerization initiator, of, if required, the at least one emulsifier, of, if required, the at least one protective colloid used and/or of the at least one monomer having at least one ethylenically unsaturated group and of, if required, the further conventional assistants and additives in a reaction container and heating the content of the reaction container to, the reaction temperature. At this temperature any remaining residual amounts of water, of the at least one organometallic compound containing the structural feature of the formula I, of the at least one polymerization initiator, of any emulsifier, of any protective colloid used and/or of the at least one monomer having at least ethylenically unsaturated group and of any further conventional assistants and additives are added continuously or batchwise while stirring and then, if required, still kept at the reaction temperature.

However, the novel process can also be carried out by initially taking a portion or the total amount of the required water, of, if required, the at least one emulsifier, of, if required, the at least one protective colloid used and/or of the at least one monomer having at least one ethylenically unsaturated group and of, if required, the further conventional assistants and additives and, if desired, a portion of the at least one organometallic compound containing the structural feature of the formula I and of the at least one polymerization initiator in a reaction container and heating the content of the reaction container to the reaction temperature. At this temperature, the total amount or any residual amount of the at least one organometallic compound containing the structural feature of the formula I and of the at least one polymerization initiator and any residual amounts of water, of any emulsifier, of any protective colloid used and/or of the at least one monomer having at least one ethylenically unsaturated group and of any further conventional assistants and additives are added continuously or batchwise while stirring and then, if required, still kept at the reaction temperature.

It is also possible initially to take a polymer seed in a portion or the total amount of the required water, of the at least one organometallic compound containing the structural feature of the formula I, of the at least one polymerization initiator, of, if required, the at least one emulsifier, of, if required, the at least one protective colloid used and/or of, if required, the further conventional assistants and additives at the reaction temperature in a reaction container. The total amount of the at least one monomer having at least one ethylenically unsaturated group and any residual amounts of water, of the at least one organometallic compound containing the structural feature of the formula I, of the at least one polymerization initiator, of any emulsifier, of any protective colloid used and/or of any further conventional assistants and additives are added continuously or batchwise, while stirring, to the reaction mixture present in the reaction container at the reaction temperature and then, if required, still kept at the reaction temperature.

In this seed procedure, it is also possible if required initially to take a portion of the at least one organometallic compound containing the structural feature of the formula I and of the at least one polymerization initiator in the reaction container as well and to add, at the reaction temperature, the total amount or the residual amount of the at least one organometallic compound containing the structural feature of the formula I and of the at least one polymerization initiator and the total amount of the at least one monomer having at least one ethylenically unsaturated group and any residual amounts of the water, of any emulsifier, of any protective colloid used and/or of any further conventional assistants and additives continuously or batchwise while stirring.

In the abovementioned procedures, however, it is also possible, in addition to or instead of the at least one organometallic compound containing the structural feature of the formula I, to use at least one organometallic compound of the formula VIII

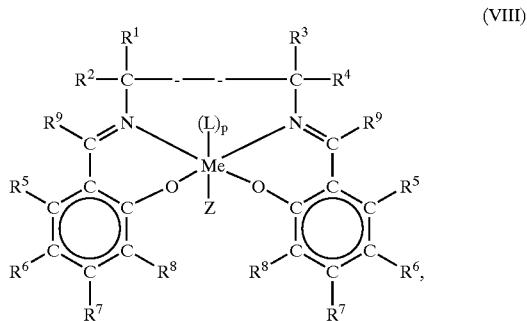

(VIII)

where Z is aryl or $C_1$- to $C_{12}$-alkyl and L and p have the abovementioned meanings.

Organometallic compounds of the formula VIII differ from organometallic compounds of the formula II only in that the metal ion is additionally bonded to an alkyl or aryl group. The bond between the metal ion and the alkyl or aryl group is thermally labile. At temperatures as are usual in the novel free radical aqueous emulsion polymerization (typically from 70 to 120° C.), the bond between the metal ion and the alkyl or aryl group is thermally cleaved and the organometallic compound of the formula II is formed in situ according to the following reaction scheme:

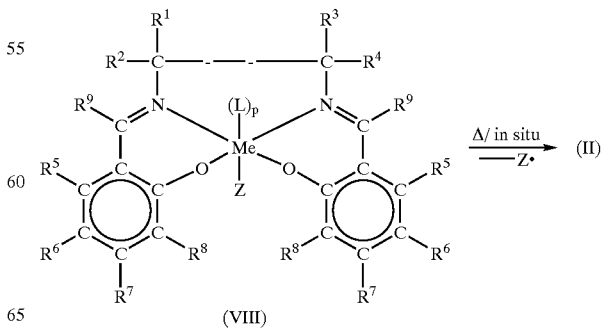

Organometallic compounds of the formula VIII are obtainable in a simple manner from the corresponding halides of the formula IX by reaction with a Grignard reagent or an alkyl- or aryllithium compound according to the following reaction scheme:

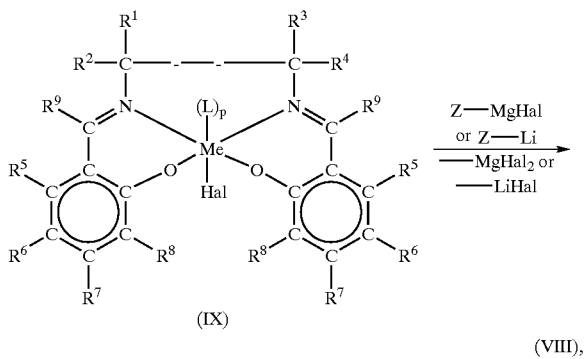

where Hal is —Cl, —Br or —I and Z is aryl or $C_1$- to $C_{12}$-alkyl and L and p have the abovementioned meanings.

An essential aspect according to the invention is that the novel process is advantageous for the preparation of aqueous dispersions of block polymers. This is possible in a simple manner by first polymerizing one type of monomer and then continuing the polymerization with another type of monomer. By further changes of monomer, it is also possible to produce polyblocks.

Of course, the residual monomers remaining in the aqueous polymer dispersion after the end of the main polymerization reaction can be removed by steam stripping and/or inert gas stripping and/or by chemical deodorization, as described, for example, in DE-A 4 419 518, EP-A 767 180 or DE-A 3 834 734, without the polymer properties of the aqueous polymer dispersion being adversely affected. It is also important that the novel organometallic compounds which have the structural feature of the formula I do not as a rule reduce the action of the microbicides which usually have to be added as preservatives to the aqueous polymer dispersions.

The at least one organometallic compound which has the structural feature of the formula I can, if required, likewise be removed from the aqueous polymer dispersion obtainable according to the invention. For example, this can be done by separating the disperse polymer from the aqueous serum by centrifuging, redispersing it by adding neutral, acidic and/or basic water, centrifuging it again, etc., the at least one organometallic compound accumulating in each case in the serum.

Alternatively, the at least one organometallic compound which has the structural feature of the formula I can be separated from the novel aqueous polymer dispersion also by coagulation and repeated washing of the coagulated polymer with neutral, acidic and/or basic water.

Aqueous polymer dispersions which contain at least one organometallic compound which has the structural feature of the formula I or which are prepared by the novel process described are very useful in particular for the preparation of adhesives, for example contact adhesives, building adhesives or industrial adhesives, binders, for example for paper coating, emulsion paints or printing inks and printing lakes for printing on plastics films, for the production of nonwovens and for the production of protective layers and water vapor barriers, for example, for priming.

EXAMPLES

General determination of the solubility of organometallic compounds of the formula II by UV/VIS spectroscopy.

At 20° C. and 1 bar (absolute), the organometallic compound of the formula II was added, while stirring, to water which contained 0.5% by weight of sodium carbonate [$Na_2CO_3$] and to styrene in each case in an amount sufficient to saturate them with the organometallic compound. Undissolved organometallic compound was filtered off over a 0.2 $\mu$m filter.

Moreover, under the abovementioned conditions, 4 calibration solutions each in water and in styrene, whose concentrations (grams of dissolved organometallic compound per 1000 g of water or styrene) were below the respective solubilities and were exactly known, were prepared with each organometallic compound investigated.

By means of UV/VIS absorption measurements of the solutions thus prepared using a UVIKON 922 spectrometer, the respective UV/VIS absorptions were measured and the respective solubilities were determined therefrom using the Beer-Lambert law.

For example, the solubilities of the following organometallic compounds of the formula II were determined:

| Organometallic compound of the formula II | Solvent 20° C., 1 bar (absolute) | Solubility in g per 1000 g of solvent |
|---|---|---|
| Compound 1 | | |
| $R^1$ to $R^8$ are each —H, the carbon atoms carrying $R^1$ to $R^4$ are linked to one another directly by means of a covalent bond, Me is $Co^{2+}$ and p is 0 ("salene-cobalt") | Water Styrene | <0.005 0.403 |
| Compound 2 | | |
| Analogous to compound 1, but $R^7$ is —OH ("hydroxysalen-cobalt") | Water Styrene | 0.630 <0.005 |
| Compound 3 | | |
| $R^5$ to $R^8$ are each —H, the radicals $R^1$ to $R^4$ together with the carbon atoms carrying them, are part of a benzene ring, Me is $Co^{2+}$ and p is 0 ("saloph-cobalt") | Water Styrene | <0.005 0.958 |
| Compound 4 | | |
| Analogous to compound 3, but $R^7$ is —OH; ("hydroxysaloph-cobalt") | Water Styrene | 0.340 <0.005 |

Carrying out the Controlled Free Radical Emulsion Polymerizations

Figure 1:
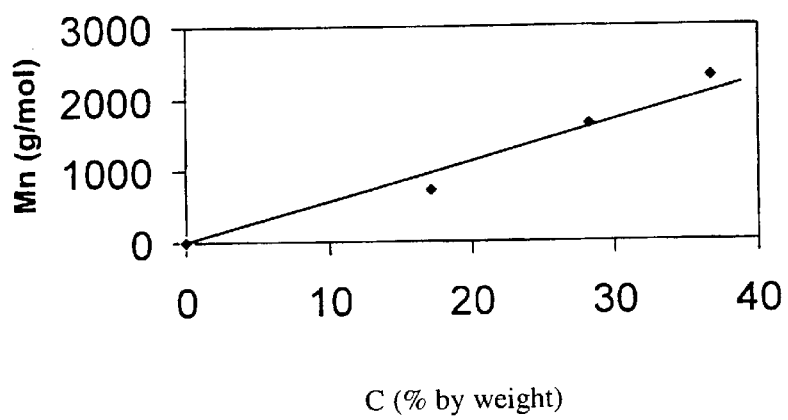
FIG. 1: Dependence of the number average molecular weight ($M_n$) on the styrene conversion (C).

1st Example 110 g of demineralized and oxygen-free water, 0.5 g of sodium dodecyl sulfate, 0.2 g of sodium carbonate and 44 mg of N,N'-bis-(2,4-dihydroxybenzylidene)-1,2-diaminobenzene (hydroxysaloph, compound of the formula VII, where $R^1$ to $R^4$ together with the carbon atoms carrying them, are part of a benzene ring, $R^5$, $R^6$, $R^8$ and $R^9$ are each H atoms and $R^7$ is OH) were initially taken while stirring, under an argon atmosphere at 20° C. and 1 bar (absolute), in a 250 ml three-necked flask (analogous to article no. 614010 of Kimble Glass Inc., 537 Crystal Avenue, Vineland, N.J. 08360, USA), equipped with a reflux condenser and a mechanical stirrer. First a solution prepared from 3 g of demineralized oxygen-free water and 36 mg of cobalt (II) acetate tetrahydrate [Co(OAc)$_2$×4 H$_2$O] and then a solution prepared from 180 mg of iodoform [HCl$_3$] and 10.3 g of oxygen-free styrene were added to the solution while stirring. The aqueous emulsion formed was heated in the absence of light to a reaction temperature of 90° C. in the course of 11 minutes. The styrene conversions then determined as a function of time, and the number average molecular weights of the polymers formed, are shown in Table 1. A plot of the number average molecular weights as a function of the styrene conversion is shown in FIG. 1. The polymers formed after 330 minutes at a styrene conversion of 36.8% by weight had a polydispersity index of 2.7 and a weight average particle diameter of 618 nm.

TABLE 1

Dependence of the styrene conversion (C) and of the number average molecular weights ($M_n$) of the polymers formed on the time (t)

| t in minutes | C in % by weight | $M_n$ in g/mol |
|---|---|---|
| 60 | 17.1 | 730 |
| 200 | 28.3 | 1650 |
| 330 | 36.8 | 2300 |

The monomer conversion was determined in general using the following formula:

$$\text{Monomer conversion}(t) = \frac{\text{dry residue}(t) - \text{dry residue}(t=0)}{\text{dry residue}(t=\infty) - \text{dry residue}(t=0)}$$

where
- dry residue (t=0): is the dry residue which was obtained from an aliquot sample of the reaction batch which was taken at the time when the reaction batch just reached the reaction temperature, extrapolated to the total batch,
- dry residue (t): is the dry residue which was obtained from an aliquot sample of the reaction batch which was taken at the time t from the reaction batch, extrapolated to the total batch,
- dry residue (t=∞): is the dry residue which would be obtained if the monomer were 100% polymerized. Theoretically, this dry residue is obtained by adding the total amount of monomers to the dry residue (t=0).

The dry residue was generally determined by drying the respective aliquot sample at 60° C. and 1 mbar to constant weight.

The respective number average molecular weight ($M_n$) and the polydispersity indices ($M_w/M_n$) of the polymers were determined by gel permeation chromatography. For this purpose, the dry residue obtained in each case was taken up in a little tetrahydrofuran, passed at 45° C., by means of a Waters 600 high pressure pump, over KF-803L and two KF-805L Shodex columns connected in series and analyzed by means of Waters 410 refractometer detectors and Waters 996 photodiode detectors. The evaluation was carried out using Millenium software.

The weight average particle diameters were generally determined by the light scattering method using AutoSizer Lo-C from Malvern Instruments Limited.

Figure 2:
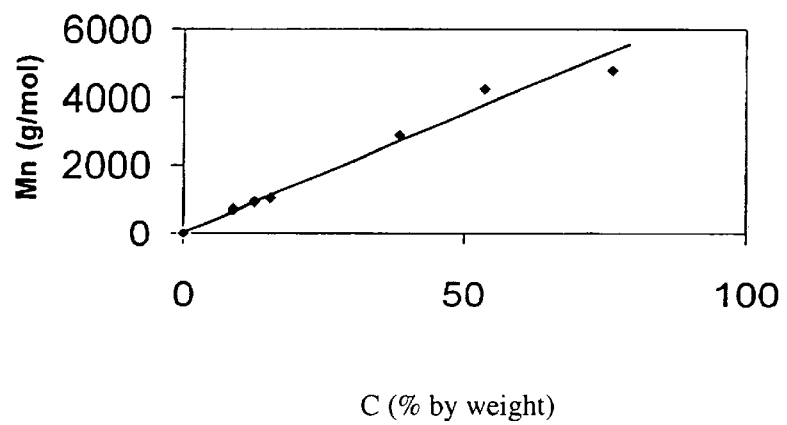
FIG. 2: Dependence of the number average molecular weight ($M_n$) on the styrene conversion (C).

2nd Example 122 g of demineralized and oxygen-free water, 1.6 g of sodium dodecyl sulfate, 0.3 g of sodium carbonate and 62 mg of hydroxysaloph were initially taken while stirring, under an argon atmosphere at 20° C. and 1 bar (absolute), in a 250 ml three-necked flask (analogous to article no. 614010 of Kimble Glass Inc.), equipped with a reflux condenser and a mechanical stirrer. First a solution prepared from 3 g of demineralized oxygen-free water and 42 mg of cobalt(II) acetate tetrahydrate and then a solution prepared from 400 mg of iodoform and 19.8 g of oxygen-free styrene were added to the solution while stirring. The aqueous emulsion formed was heated in the absence of light to a reaction temperature of 95° C. in the course of 11 minutes. The styrene conversions then determined as a function of time, and the number average molecular weights of the polymers formed, are shown in Table 2. A plot of the number average molecular weight of the polymers formed as a function of the styrene conversion is shown in FIG. 2. The polymers formed after 720 minutes at a styrene conversion of 76.5% by weight had a polydispersity index of 1.6 and a weight average particle diameter of 102 nm.

TABLE 2

Dependence of the styrene conversion (C) and of the number average molecular weights ($M_n$) of the polymers formed on the time (t)

| t in minutes | C in % by weight | $M_n$ in g/mol |
|---|---|---|
| 15 | 8.8 | 700 |
| 55 | 12.5 | 900 |
| 95 | 15.2 | 1000 |
| 210 | 38.5 | 2850 |
| 320 | 53.8 | 4250 |
| 720 | 76.5 | 4800 |

Figure 3:
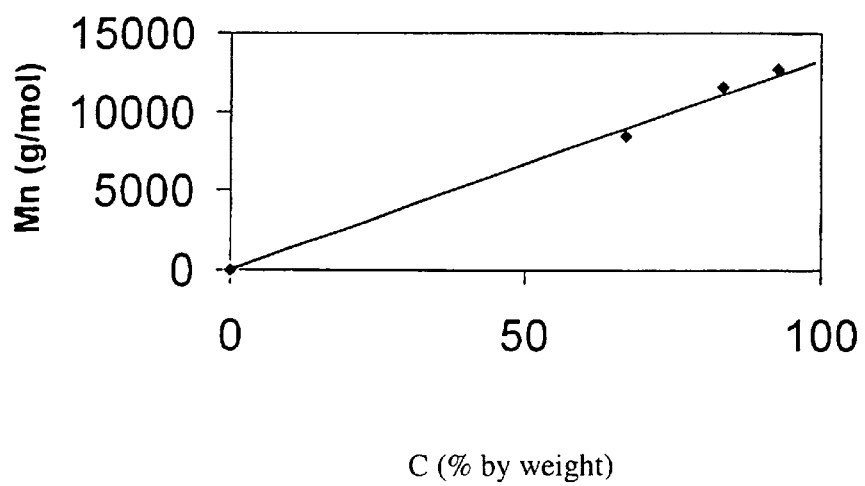
FIG. 3: Dependence of the number average molecular weight ($M_n$) on the MMA conversion (C).

3rd Example 121 g of demineralized and oxygen-free water, 1.7 g of sodium dodecyl sulfate, 0.3 g of sodium carbonate and 62 mg of hydroxysaloph were initially taken while stirring, under an argon atmoshere at 20° C. and 1 bar (absolute), in a 250 ml three-necked flask (analogous to article no. 614010 of Kimble Glass Inc.), equipped with a reflux condenser and a mechanical stirrer. First a solution prepared from 3 g of demineralized oxygen-free water and 42 mg of cobalt(II) acetate tetrahydrate and then a solution prepared from 400 mg of iodoform and 11.7 g of oxygen-free methyl methacrylate (MMA) were added to the solution while stirring. The aqueous emulsion formed was heated in the absence of light to a reaction temperature of 80° C. in the course of 11 minutes. The MMA conversions then determined as a function of time, and the number average molecular weights of the polymers formed, are shown in Table 3. A plot of the number average molecular weights of the polymers formed as a function of the MMA conversion is shown in FIG. 3. The polymers formed after 355 minutes at an MMA conversion of 92.8% by weight had a polydispersity index of 2.1 and a weight average particle diameter of 77 nm.

TABLE 3

Dependence of the MMA conversion (C) and of the number average molecular weights ($M_n$) of the polymers formed on the time (t)

| t in minutes | C in % by weight | $M_n$ in g/mol |
|---|---|---|
| 105 | 67.2 | 8500 |
| 180 | 83.5 | 11600 |
| 355 | 92.8 | 12700 |

Figure 4:
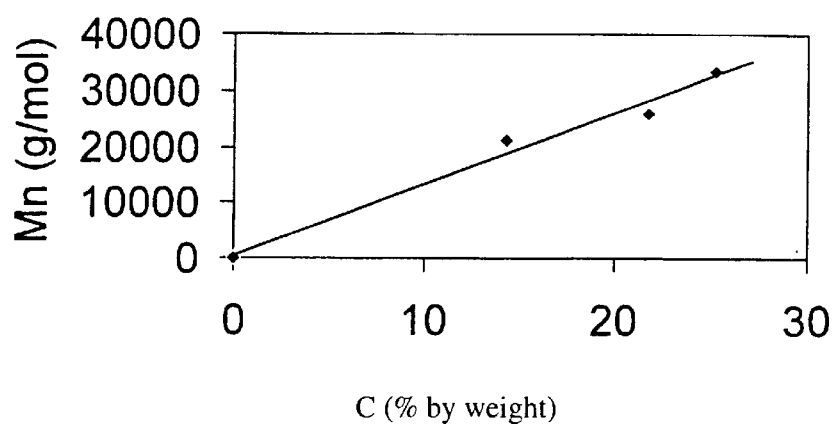
FIG. 4: Dependence of the number average molecular weight ($M_n$) on the MMA conversion (C).

4th Example 158 g of demineralized and oxygen-free water, 1.0 g of sodium dodecyl sulfate, 0.3 g of sodium carbonate and 52 mg of hydroxysaloph were initially taken while stirring, under an argon atmosphere at 20° C. and 1 bar (absolute), in a 250 ml three-necked flask (analogous to article no. 614010 of Kimble Glass Inc.), equipped with a reflux condenser and a mechanical stirrer. First a solution prepared from 3 g of demineralized oxygen-free water and 42 mg of cobalt(II) acetate tetrahydrate and then a solution prepared from 270 mg of 1-iodoethyl acetate and 12.7 g of oxygen-free MMA were added to the solution while stirring. The aqueous emulsion formed was heated in the absence of light to a reaction temperature of 80° C. in the course of 11 minutes. The MMA conversions then determined as a function of time, and the number average molecular weights of the polymers formed, are shown in Table 4. A plot of the number average molecular weights of the polymers formed as a function of the MMA conversion is shown in FIG. 4. The polymers obtained after 60 minutes at an MMA conversion of 25.2% by weight had a polydispersity index of 1.8.

TABLE 4

Dependence of the MMA conversion (C) and of the number average molecular weights ($M_n$) of the polymers formed on the time (t)

| t in minutes | C in % by weight | $M_n$ in g/mol |
|---|---|---|
| 10 | 14.3 | 21100 |
| 25 | 21.7 | 26000 |
| 60 | 25.2 | 33300 |

Figure 5:
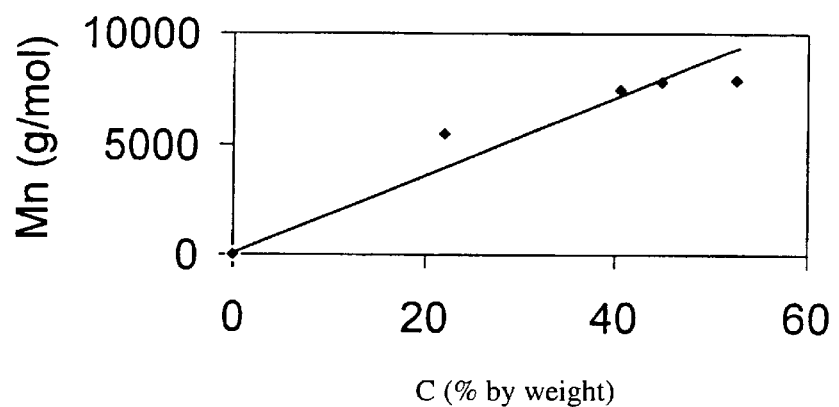
FIG. 5: Dependence of the number average molecular wight ($M_n$) on the MMA conversion (C).

5th Example 160 g of demineralized and oxygen-free water, 1.0 g of sodium dodecyl sulfate, 0.1 g of sodium carbonate and 94 mg of hydroxysaloph were initially taken while stirring, under an argon atmosphere at 20° C. and 1 bar (absolute), in a 250 ml three-necked flask (analogous to article no. 614010 of Kimble Glass Inc.), equipped with a reflux condenser and a mechanical stirrer. First a solution prepared from 3 g of demineralized oxygen-free water and 65 mg of trichromium dihydroxyheptaacetate [$Cr_3(OH)_2(OAc)_7$] and then a solution prepared from 400 mg of iodoform and 12.0 g of oxygen-free MMA were added to the solution while stirring. The aqueous emulsion formed was heated in the absence of light to a reaction temperature of 80° C. in the course of 11 minutes. The MMA conversions then determined as a function of time, and the number average molecular weights, are shown in Table 5. A plot of the number average molecular weights of the polymers formed as a function of the MMA conversion is shown in FIG. 5. The polymers formed after 150 minutes had a polydispersity index of 2.4 and a weight average particle diameter of 150 nm.

TABLE 5

Dependence of the MMA conversion (C) and of the number average molecular weights ($M_n$) of the polymers formed on the time (t)

| t in minutes | C in % by weight | $M_n$ in g/mol |
|---|---|---|
| 10 | 22.0 | 5500 |
| 50 | 40.5 | 7500 |
| 70 | 44.9 | 7800 |
| 150 | 52.5 | 7900 |

6th Example 128 g of demineralized and oxygen-free water, 0.8 g of sodium dodecyl sulfate, 0.3 g of sodium carbonate and 45 mg of N,N'-bis-(2,4-dihydroxybenzylidene)-1,2-diaminoethane (hydroxysalen; compound of the formula VII where $R^7$ to $R^6$ and $R^8$ and $R^9$ are each H atoms and $R^7$ is OH and the carbon atoms carrying $R^1$ to $R^4$ are linked to one another directly via a covalent bond) were initially taken while stirring, under an argon atmosphere at 20° C. and 1 bar (absolute), in a 250 ml three-necked flask (analogous to article no. 614010 of Kimble Glass Inc.), equipped with a reflux condenser and a mechanical stirrer. First a solution prepared from 3 g of demineralized oxygen-free water and 38 mg of cobalt(II) acetate tetrahydrate and then a solution prepared from 300 mg of iodoform and 11.0 g of oxygen-free styrene were added to the solution while stirring. The aqueous emulsion formed was heated in the absence of light to a reaction temperature of 90° C. in the course of 11 minutes. After 520 minutes, a monomer conversion of 52% by weight was achieved. The polymers formed had a number average molecular weight of 32000 g/mol, a weight average particle diameter of 267 nm and a polydispersity index of 2.0.

1st Comparative Example 108 g of demineralized and oxygen-free water, 1.0 g of sodium dodecyl sulfate, 0.3 g of sodium carbonate and 36 mg of cobalt(II) acetate tetrahydrate were initially taken while stirring, under an argon atmosphere at 20° C. and 1 bar (absolute), in a 250 ml three-necked flask (analogous to article no. 614010 of Kimble Glass Inc.), equipped with a reflux condenser and a mechanical stirrer. A solution prepared from 12.0 g of oxygen-free styrene, 44 mg of N,N'-bis(2-hydroxybenzylidene)-1,2-diaminobenzene (saloph; compound of the formula VII where $R^1$ to $R^4$ together with the carbon atoms carrying them, are part of a benzene ring, and $R^5$ to $R^9$ are each H atoms) and 210 mg of iodoform was added to this. The aqueous emulsion formed was heated in the absence of light to a reaction temperature of 90° C. in the course of 11 minutes. After 10 minutes, the emulsion had completely coagulated. No dispersed polymer particles were detectable in the aqueous phase.

2nd Comparative Example 110 g of demineralized and oxygen-free water, 0.5 g of sodium dodecyl sulfate, 0.2 g of sodium carbonate and 36 mg of cobalt(II) acetate tetrahydrate were initially taken while stirring, under an argon atmosphere at 20° C. and 1 bar (absolute), in a 250 ml three-necked flask (analogous to article no. 614010 of Kimble Glass Inc.), equipped with a reflux condenser and a mechanical stirrer. A solution prepared from 12.5 g of oxygen-free styrene, 44 mg of N,N-bis(2-hydroxybenzylidene)-1,2-diaminoethane (salen; compound of the formula VII, where $R^1$ to $R^9$ are each H atoms and the carbon atoms carrying $R^1$ to $R^4$ are bonded to one another directly via a covalent bond) and 180 mg of 1-bromoethylbenzene was added to this. The aqueous emulsion formed was heated in the absence of light to a reaction temperature of 90° C. in the course of 11 minutes. After 10 minutes, the emulsion had completely coagulated. No dispersed polymer particles were detectable in the aqueous phase.

3rd Comparative Example 110 g of demineralized and oxygen-free water, 0.5 g of sodium dodecyl sulfate, 0.2 g of sodium carbonate, 36 mg of cobalt(II) acetate tetrahydrate and 44 mg of salen were initially taken while stirring, under an argon atmosphere at 20° C. and 1 bar (absolute), in a 250 ml three-necked flask (analogous to article no. 614010 of Kimble Glass Inc.), equipped with a reflux condenser and a mechanical stirrer. A solution prepared from 12.5 g of oxygen-free styrene and 180 mg of 1-bromoethylbenzene was added to this. The aqueous emulsion formed was heated in the absence of light to a reaction temperature of 90° C. in the course of 11 minutes. After 10 minutes, the emulsion had completely coagulated. No dispersed polymer particles were detectable in the aqueous phase.

4th Comparative Example 122 g of demineralized and oxygen-free water, 0.8 g of sodium dodecyl sulfate, 0.6 g of sodium carbonate and 36 mg of iron(II) acetate [Fe(OAc)$_2$] were initially taken while stirring, under an argon atmosphere at 20° C. and 1 bar (absolute), in a 250 ml three-necked flask (analogous to article no. 614010 of Kimble Glass Inc.), equipped with a reflux condenser and a mechanical stirrer. A solution prepared from 12.0 g of oxygen-free styrene, 46 mg of salen and 200 mg of iodoform was added to this. The aqueous emulsion formed was heated in the absence of light to a reaction temperature of 90° C. in the course of 11 minutes. After 10 minutes, the emulsion had completely coagulated. No dispersed polymer particles were detectable in the aqueous phase.

5th Comparative Example 144 g of demineralized and oxygen-free water, 1.2 g of sodium dodecyl sulfate, 0.4 g of sodium carbonate and 35 mg of cobalt(II) acetate tetrahydrate were initially taken while stirring, under an argon atmosphere at 20° C. and 1 bar (absolute), in a 250 ml three-necked flask (analogous to article no. 614010 of Kimble Glass Inc.), equipped with a reflux condenser and a mechanical stirrer. A solution prepared from 13.5 g of oxygen-free MMA, 51 mg of salen and 240 mg of 1-bromoethylbenzene was added to this. The aqueous emulsion formed was heated in the absence of light to a reaction temperature of 90° C. in the course of 11 minutes. After 10 minutes, the emulsion had completely coagulated. No dispersed polymer particles were detectable in the aqueous phase.

We claim:

1. A process comprising:
   dispersing at least one chemical compound having at least one ethylenically unsaturated group in an aqueous medium and
   polymerizing the compound with at least one free radical polymerization initiator in the presence of at least one organometallic compound, wherein the organometallic compound has the following structural feature of formula I,

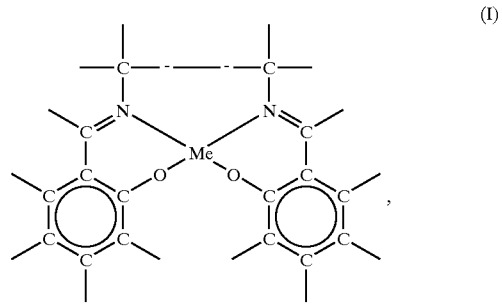

where:
Me is a metal ion,

┄┄┄ is a covalent bond or a monoatomic to triatomic covalent, bridging chain, not including the atoms bonded to the chain, and is a covalent bond to a neighboring atom,
wherein the organometallic compound has a solubility in acidic, basic, or neutral water at 20° C. and 1 bar absolute greater than the solubility in styrene,
wherein the polymerizing is a free radical-initiated aqueous emulsion polymerization, and
wherein said process provides an aqueous polymer dispersion.

2. A process as claimed in claim 1, wherein the organometallic compound is a compound of formula II

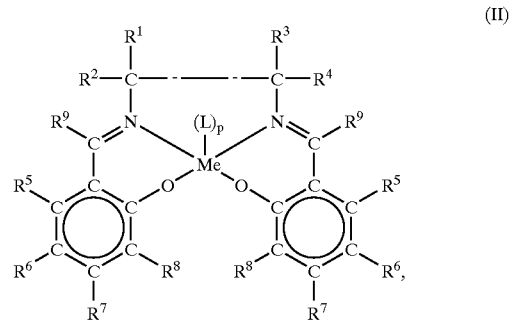

where:
$R^1$, $R^2$, $R^3$, $R^4$ independently of one another, are each —H, —CO$_2$M$^1$, where M$^1$ is —H, an alkali metal, ammonium or —(CH$_2$CH$_2$O—)$_m$M$^2$, where M$^2$ is —H, an alkali metal or ammonium and m is from 1 to 1000, —PO$_3$HM$^1$, —PO$_3$M$^3$M$^4$, where M$^3$ and M$^4$ independently of one another are each an alkali metal, ammonium, C$_1$- to C$_{12}$-alkyl or substituted alkyl, in which up to four H atoms of the alkyl radical are replaced by —OM$^1$, —SM$^1$, —CO$_2$M$^1$, —NH$_2$, a quaternized nitrogen atom, —SO$_3$M$^1$ and/or —OSO$_3$M$^1$, or —CH$_2$O—(CH$_2$CH$_2$O—)$_m$M$^2$, and $R^1$ and/or $R^3$ independently of $R^2$ and $R^4$, may be —CN, and $R^2$ and $R^4$, together with the carbon atoms carrying them and directly linked by a covalent bond, independently of $R^1$ and $R^3$, can form an aliphatically saturated, an aliphatically partly unsaturated or an aromatically saturated ring which can additionally contain from 1 to 3 hetero atoms, selected from the group consisting of N, O, S and P with, the number of ring atoms being from 5 to 10, $R^5, R^6, R^7, R^8$ independently of one another are each —H, —F, —Cl, —Br, —I, —NO$_2$, —CHO, —SM$^1$, —OM$^1$, —SO$_3$M$^1$, —CO$_2$M$^1$, —CN, —SCN, —PO$_3$HM$^1$, —PO$_3$M$^3$M$^4$, —OSO$_3$M$^1$, —OPO$_3$HM$^1$, —OPO$_3$M$^3$M$^4$, —NR$^{10}$R$^{11}$, where R$^{10}$ and R$^{11}$ independently of one another, are each —H or C$_1$- to C$_6$-alkyl, —SiR$^{12}$R$^{13}$R$^{14}$, where R$^{12}$, R$^{13}$ and R$^{14}$ independently of one another, are each C$_1$- to C$_6$-alkyl or C$_1$- to C$_6$-alkoxy, —OR$^{15}$, —SR$^{15}$, —CO$_2$R$^{15}$, —PO$_3$HR$^{15}$, —PO$_3$R$^{15}$R$^{16}$, where R$^{15}$ and R$^{16}$, independently of one another, are each C$_1$- to C$_3$-alkyl or C$_2$- to C$_6$-alkyl, in which up to four H atoms of the alkyl radical are replaced by —OM$^1$, —SM$^1$, —CO$_2$M$^1$, —NH$_2$, a quaternized nitrogen atom, —SO$_3$M$^1$ and/or —OSO$_3$M$^1$, —CH$_2$O—(CH$_2$CH$_2$O—)$_m$M$^2$, C$_1$- to C$_{10}$-alkyl, in which at least half the carbon atoms are replaced by at least one substituent from the group consisting of —OM$^1$, —SM$^1$, —CO$_2$M$^1$, —NH$_2$, a quaternized nitrogen atom, —SO$_3$M$^1$ and —OSO$_3$M$^1$, C$_2$- to C$_{10}$-alkenyl, in which up to three H atoms are replaced by —OM$^1$, —SM$^1$, —CO$_2$M$^1$, —NH$_2$, a quaternized nitrogen atom, —SO$_3$M$^1$ and/or —OSO$_3$M$^1$, and two of the radicals R$^5$, R$^6$, R$^7$ and R$^8$, which are carried by neighboring carbon atoms, together with the carbon atoms carrying them and independently of the other radicals, can form an aliphatically saturated, an aliphatically partly unsaturated or an aromatically saturated ring which can additionally contain from 1 to 3 hetero atoms selected from the group consisting of N, O, S and P, with the number of ring atoms being 5 or 6, and the two radicals R$^7$ and/or the two radicals R$^8$, in each case with the carbon atoms carrying these radicals, can form a 5- or 6-atom covalent, bridging chain, not including the atoms bonded to the chain members, R$^9$ is —H,

——— is either a covalent bond or a covalent, bridging chain of up to three atoms, the atoms bonded to the chain members not being included, Me is a metal ion, L is a Lewis base and p is 0, 1 or 2.

3. The process as claimed in claim 1, wherein the metal ion is present in at least two oxidation states.

4. A process as claimed in claim 1, wherein Me is selected from the group consisting of Fe$^{2+}$, Fe$^{3+}$, Ru$^{2+}$, Ru$^{3+}$, Cr$^{2+}$, Cr$^{3+}$, Mo$^{2+}$, Mo$^{3+}$, W$^{3+}$, W$^{3+}$, Co$^{2+}$, Co$_{3+}$, Re$^{2+}$, Re$^{3+}$, V$^{2+}$, V$^{3+}$, Mn$^{2+}$, Mn$^{3+}$, Zr$^{2+}$, Zr$^{3+}$, Zr$^{4+}$, Ti$^{2+}$, Ti$^{3+}$, Ti$^{4+}$, Ce$^{2+}$ and Ce$^{3+}$.

5. A process as claimed in claim 2, wherein L is selected from the group consisting of water, tetrahydrofuran, dioxane, pyridine, ammonia, primary amines, secondary amines, tertiary amines, trialkylphosphine, trialkoxyphosphine, triarylphosphine and triaryloxyphosphine.

6. A process as claimed in claim 1, further comprising adding a portion or the total amount of the organometallic compound to the aqueous medium before, with, or after the monomers are added.

7. A process as claimed in claim 1, further comprising producing a portion or the total amount of the organometallic compound in situ in the aqueous medium before, during or after the monomers are added.

8. A process as claimed in claim 1, wherein the free radical polymerization initiator is of formula III,

(III)

where:

X is —Cl, —Br, —I, —OR$^{20}$, wherein R$^{20}$ is C$_1$- to C$_{20}$-alkyl, in which up to one third of the H atoms may, independently of one another, be replaced by —Cl, —Br or —I, —SR$^{21}$, —SeR$^{21}$, —OC(=O)R$^{21}$, —OP(=O)R$^{21}$, —OP(=O)(OR$^{21}$)$_2$, —OP(=O)OR$^{21}$, —ON(R$^{21}$)$_2$, —SC(=S)N(R$^{21}$)$_2$, or —SC(=S)R$^{21}$, wherein R$^{21}$ is -aryl or C$_1$- to C$_{20}$-alkyl and, in the case of —ON(R$^{21}$)$_2$, the two groups R$^{21}$ with the N atom carrying them may form a 5- or 6-membered heterocyclic ring, and R$^{17}$, R$^{18}$, R$^{19}$ independently of one another, are each —H, —Cl, —Br, —I, —CO$_2$H, —CN, —CO$_2$R$^{21}$, or C$_1$- to C$_{20}$-alkyl, which may be unsubstituted or substituted, C$_3$- to C$_8$-cycloalkyl, which may be unsubstituted or substituted, -aryl, which may be unsubstituted or substituted, -aralkyl, which may be unsubstituted or substituted, or heterocyclyl, which may be unsubstituted or substituted.

9. A process as claimed in claim 8, wherein X is —Cl, —Br or —I.

10. A process as claimed in claim 1, wherein the molar ratio of the organometallic compound to the polymerization initiator is from 0.00001:1 to 10:1.

11. A process as claimed in claim 1, wherein the molar ratio of the monomers to the organometallic compound is ≧1.

12. The process as claimed in claim 2, wherein the metal is present in at least two oxidation states.

13. The process as claimed in claim 12, wherein Me is selected from the group consisting of Fe$^{2+}$, Fe$^{3+}$, Ru$^{2+}$, Ru$^{3+}$, Cr$^{2+}$, Cr$^{3+}$, Mo$^{2+}$, Mo$^{3+}$, W$^{2+}$, W$^{3+}$, Co$^{2+}$, Co$^{3+}$, Re$^{2+}$, Re$^{3+}$, V$^{2+}$, V$^{3+}$, Mn$^{2+}$, Mn$^{3+}$, Zr$^{2+}$, Zr$^{3+}$, Zr$^{4+}$, Ti$^{2+}$, Ti$^{3+}$, Ti$^{4+}$, Ce$^{2+}$ and Ce$^{3+}$.

14. A process as claimed in claim 12, wherein L is selected from the group consisting of water, tetrahydrofuran, dioxane, pyridine, ammonia, primary amines, secondary amines, tertiary amines, trialkylphosphine, trialkoxyphosphine, triarylphosphine and triaryloxyphosphine.

15. A process as claimed in claim 13, wherein L is selected from the group consisting of water, tetrahydrofuran, dioxane, pyridine, ammonia, primary amines, secondary amines, tertiary amines, and trialkylphosphine, trialkoxyphosphine, triarylphosphine and triaryloxyphosphine.

16. The process as claimed in claim 2, wherein R$^7$ of formula II is OH.

* * * * *